United States Patent
Hildebrand (10) Patent No.: US 7,052,486 B2
(45) Date of Patent: May 30, 2006

(54) METHOD AND SYSTEM FOR TREATING DEPRESSIVE AND ANXIETY DISORDERS

(75) Inventor: Keith Robert Hildebrand, Houlton, WI (US)

(73) Assignee: Medtronic, Inc., Minneapolis, MN (US)

(\*) Notice: Subject to any disclaimer, the term of this patent is extended or adjusted under 35 U.S.C. 154(b) by 213 days.

(21) Appl. No.: 10/335,832

(22) Filed: Jan. 2, 2003

(65) Prior Publication Data

US 2004/0133184 A1 Jul. 8, 2004

(51) Int. Cl.
*A61M 31/00* (2006.01)

(52) U.S. Cl. .................................. 604/502; 604/508
(58) Field of Classification Search ............... 604/500, 604/502, 503, 20.22, 890.1–892.1, 65, 508; 607/62, 116

See application file for complete search history.

(56) References Cited

U.S. PATENT DOCUMENTS

| 3,882,245 | A | * | 5/1975 | Du Charme | ................. | 514/559 |
| 5,599,560 | A | | 2/1997 | Siuciak | | |
| 6,176,242 | B1 | * | 1/2001 | Rise | ........................... | 128/898 |

OTHER PUBLICATIONS

Sussman, N., (1994), "The Potential Benefits of Serotonin Receptor-Specific Agents," *J Clin Psychiatry* 55: 45-51.

Thase, M.E., Frazer, A., Gorman, J.M., Hirschfeld, R.M. and Roose, S.P., (2000), "Pharmacotherapy of Depression: New Strategies," *A Symposium of the American Psychiatric Association 2000 Annual Meeting*.

Howe, J. and Yaksh, T.L. (1982), "Changes in Sensitivity to Intrathecal Norepinephrine and Serotonin after 6-Hydroxydopamine, 5, 6-Dihydroxytryptamine or Repeated Monoamine Administration," *J Pharmacol Exp Ther* 220: 311-321.

Borszcz, George S., Johnson, Christine P., and Williams, Daniel H."Increases in Vocalization and Motor Reflex Theresholds Generated by the Intrathecal Administration of Serotonin or Norepinephrine," *Behavioral Neuroscience*, (1996) vol. 110, No. 4, 809-822.

Milne, B$^2$, Cervenko, F., Jhamandas, K., Loomis C. and Sutak, M., (1985), "Analgesia and Tolerance to Intrathecal Morphine and Norepinephrine Infusion via Implanted Mini-osmotic Pumps in the Rat," *Pain* 22: 165-172.

Minor, B.G.$^1$, Persson, M.$^1$, Post, C.$^1$, Jonsson G.$^1$ (1988), "Intrathecal Noradrenaline Restores 5-Methoxy-N, N-dimethyltryptamine Induced Antinociception Abolished by Intrathecal 6-Hydroxydopamine," *J Neural Trasm* 72: 107-120.

(Continued)

*Primary Examiner*—Kevin C. Sirmons
(74) *Attorney, Agent, or Firm*—Banner & Witcoff, Ltd.

(57) ABSTRACT

A method and system for treating depressive and anxiety disorders is disclosed. The method and system of the present invention comprises operating a programmable pump for the delivery of at least one therapeutic substance into the cerebrospinal fluid of a patient for the treatment of depressive or anxiety disorders. In an embodiment, a sensor implanted in a patient may be used in combination with the programmable pump and catheter.

9 Claims, 5 Drawing Sheets

OTHER PUBLICATIONS

Brustein, E. and Rossignol, S. (1999), "Recovery of Locomotion After Ventral and Ventrolateral Spinal Lesions in the Cat. II. Effects of Noradrenergic and Serotoninergic Drugs," *American Physiological Society* 1513-1530.

Weisenfeld-Hallin, Z., (1987), "Intrathecal Noradrenaline has a Dose-Dependent Inhibitory or Facilitatory Effect on the Flexion Reflex in the Rat," *Acta Physiol Scand* 130: 507-511.

Leonard, B.E., (1997). "Noradrenaline in Basic Models of Depression," *Eur Neuropsychophamacol* 7: S11-S16.

Kramer, M.S., et al.(1998), "Distinct Mechanism for Antidepressant Activity by Blockade of Central Substance P Receptors," *Science* vol. 281 Sep. 11, 1640-1625.

Keller, M.B., Schatzberg, A.F., Charney, D.S. Krishnan, K.R.,Weissman, M.M. and Nemeroff, C.B. (2000), "Novel Treatments of Depression," *A symposium held at the 2000 Annual Meeting of the APA*.

Arborelius, L., M J Owens, P M Plotsky and C B Nemeroff, "The role of corticotropin-releasing factor in depression and anxiety disorders", *Journal of Endocrinology* (1999) 160; 1-12.

Carl Salzman, M.D. "Substance P in Depression", *Harvard Health Publications*; Dec. 2001.

Bender, Kenneth J., Pharm. D., M.A., "Substance P'Antagonist Relieves Depression," *Psychiatric Times*, (Nov. 1998) vol. XV, issue 11.

Theodore L. Munsat, M.D., James Taft, PA-C and Ivor M.D. Jackson, M.D., "Pharmacokinetics of intrathecal thyrotropin-releasing hormone", *Neurology* (1987) 37:597-601.

Albert Sattin, "A Heuristic Model of Mental Depression Derived from Basic and Applied Research on Thyrotropin-Releasing Hormone," *THYROID*, vol. 8, No. 10 (1998).

Potter, William Z, and Manji, Husseini K., "Catecholamines in Depression: An Update," *Clinical Chemistry* vol. 40, No. 2 (1994).

Brian E. Leonard, "The role of noradrenaline in depression: a review", *Journal of Psychopharmacology*, vol. II No. 4 (1997) 539-547.

Cleare, A.J., Murray, M., Sherwood, R.A. and O'Keane V., "Abnormal 5-HT$_{1D}$ receptor function in major depression: a neuropharmacological challenge study using sumatriptan," *Psychological Medicine* (1998) 28: 295-300.

Spina M.G., et al, "Behavioral effects of central administration of the novel CRF antagonist astressin in rats," *Neuropsychopharmacology*, Mar 22, 2000 (3) 230-9.

"Depression," *National Institute of Mental Health*, Publication No. 00-3561 (2000).

Janicak, P.G. and Martis, B. (1998), "Strategies for Treatment-Resistant Depression", *Clinical Cornerstore* 1:58-71.

Shelton, R.C. (1999), "Treatment Options for Refractory Depression," *J Clin. Psychiatry* 60:57-63.

Joffe, R.T. (1997), "Refractory Depression: Treatment Strategies, with Particular Reference to the Thyroid Axis," *J. Psychiatry Neurosci.* 22:327-331.

"Anxiety Disorders," *National Institute of Mental Health, Publication No. 00-3879* (2000).

Walter, G., Rey, J.M., and Mitchel, P.B. (1999), "Practitioner Review: Electroconvulsive Therapy in Adolescents," *J. Child Psychiatry* 40: 325-334.

Sackeim, H. A., Prudic, J., et al. (1990) "The Impact of Medication Resistance and Continuation Pharmacotherapy on Relapse Following Response To Electroconvulsive Therapy in Major Depression," *J Clin Psychopharmacol* 10:96-104.

ITIL, T.M., Patterson, C.D., Polvan, N., Bigelow, A. and Bergey, B. (1975), "Clinical and CNS Effects of Oral and I.V. Thyrotropin-Releasing Hormone in Depressed Patients," *Dis Nerv Sys* 2: 529-536.

Prange, A.J., Wilson, I.C., Lara, P.P., Alltop, L.B. and Breese, G.R. (1972), "Effects of Thyrotropin-Releasing Hormone in Depression," *Lancet* 2:999-1002.

Callahan, A.M., Frye, M.A., Marangell, L.B., George, M.S. Ketter, T.A., L'Herrou, T.A. and Post R.M., (1997), "Comparative Antidepressant Effects of Intravenous and Intrathecal Thyrotropin-Releasing Hormone: Confounding Effects of Tolerance and Implications for Therapeutics," *Biol. Psychiatry* 41: 264-272.

Marangell, L.B., George, M. S., Callahan, A.M., Ketter, T.A., Pazzaglia, P.J., L'Herrou, T.A., Leverich, G.S. and Post, R.M., (1997), "Effects of Intrathecal Thyrotropin-Releasing Hormone (Protirelin) in Refractory Depressed Patients," *Arch. Gen. Psychiatry* 54:214-222.

Stern L., Zohar, J., Cohen, R., and Sasson, Y., (1998), "Treatment of Severe, Drug Resistant Obsessive Compulsive Disorder with 5HT$_{1D}$ agonist Sumatriptan," *Eur Neuropsychopharmacol* 8: 325-328.

Saxena, P.R. (1991), "Migraine Therapy and 5-HT Receptor Activity," *J Neurol* 238: S36-S37.

Arranz, B., Eriksson, A., Mellerup, E., Plenge, P. and Marcusson, J., (1994), "Brain 5HT$_{1A}$,5HT$_{1D}$,and 5HT$_2$Receptors in Suicide Victims," *Biol Psychiatry* 35: 457-463.

Deakin, J.F.W., (1988), "5HT$_2$ Receptors, Depression and Anxiety," *Pharmacol Biochem Behav* 29: 819-830.

Feighner, J.P., (1999), "Mechanism of Action of Antidepressant Medications," *J Clin Psychiatry* 60: 4-13.

Ruoff, G.E., (1996), "Depression in the Patient with Chronic Pain," *J Fam Pract* 43: S25-S34.

* cited by examiner

METHOD AND SYSTEM FOR TREATING DEPRESSIVE AND ANXIETY DISORDERS

FIELD OF THE INVENTION

This invention relates to a method and system for treating depressive and anxiety disorders by means of a programmable pump and a catheter for the delivery of a therapeutic substance into the cerebrospinal fluid of a patient.

BACKGROUND OF THE INVENTION

Depressive disorders are common illnesses that affect more than 18.8 million Americans. "Depression," *National Institute of Mental Health*, Publication No. 00-3561 (2000). Depressive disorders, as with other illnesses, come in different forms. Three of the more common depressive disorders include major depression, dysthymia, and bipolar disorder. Major depression is manifested by a combination of symptoms that interfere with a person's ability to function normally, including the ability to work, study, or sleep. Such disabling episodes of depression may occur only, once but more commonly occur several times in a person's lifetime. Dysthymia, a less severe type of depression, involves long term chronic symptoms that do not disable a person but keep a patient from functioning well or feeling good. Bipolar disorder is a form of depression that is characterized by cycling mood changes.

Significant portions of patients treated for depressive disorders do not respond to therapies presently available (i.e., electroconvulsive therapy (ECT), psychotherapy, and orally delivered antidepressant medications, or various combinations of all three therapies). This shortcoming exists despite the introduction of a variety of new more specific and significantly safer medications to the market place (e.g., Prozac®, Zoloft®, Paxil®). Approximately 20–30% of patients treated for depression with antidepressant medications fall into the category of being treatment-resistant. Janicak, P. G. and Martis, B. (1998), "Strategies for Treatment-Resistant Depression," *Clinical Cornerstone* 1:58–71; Shelton, R. C. (1999), "Treatment Options for Refractory Depression," *J Clin. Psychiatry* 60:57–63; Joffe, R. T. (1997), "Refractory Depression: Treatment Strategies, with Particular Reference to the Thyroid Axis," *J. Psychiatry Neurosci.* 22:327–331. Moreover, 30% to 50% of patients do not respond to their initial medication regardless of which class of drug is chosen. The treatment-resistant population consists of patients who have been treated unsuccessfully with multiple drug trials using different classes of orally administered antidepressants, psychotherapy, and potentially ECT.

Similar to depressive disorders, anxiety disorders affect approximately 19 million American adults. "Anxiety Disorders," *National Institute of Mental Health*, Publication No. 00-3879 (2000). Anxiety disorders are serious medical illnesses that afflict people's lives with overwhelming anxiety and fear. There are many different anxiety disorders that include panic disorder, obsessive-compulsive disorder, social phobia, and generalized anxiety disorder. Though each of these forms of anxiety disorders may have its own distinct features, they all involve an excessive, irrational fear and/or dread.

Similar to results for the treatment of depressive disorders, a significant portion of patients treated for anxiety disorders do not respond to therapies presently available (i.e., electroconvulsive therapy (ECT), psychotherapy, and orally delivered antidepressant medications, or various combinations of all three). This shortcoming exists despite the introduction of a variety of new more specific and significantly safer medications to the market place.

ECT

A method of treatment for patients who have failed to respond to several classes of therapeutics is ECT. Unfortunately, ECT also has a failure rate of approximately 30–40%. Walter, G., Rey, J. M., and Mitchell, P. B. (1999), "Practitioner Review: Electroconvulsive Therapy in Adolescents," *J Child Psychiatr* 40: 325–334. ECT is a therapy that has been steadily increasing in use despite the stigma associated with its historical misuse in psychiatric medicine. ECT is now generally accepted by the American Psychiatric Association and the National Institute of Mental Health as being a safe and effective therapy for major depression. The side effects associated with ECT are generally mild and include headache, myalgia, nausea, memory problems, and confusion. Walter, G., Rey, J. M., and Mitchell, P. B. (1999), "Practitioner Review: Electroconvulsive Therapy in Adolescents," *J Child Psychiatr* 40: 325–334. Unfortunately, a small percentage of the ECT-treated patients experience significant cognitive impairments (pre- and/or post treatment memory deficits of durations of weeks to months), manic switching, and tachycardia such that treatment must be discontinued. In addition, ECT requires general anesthesia and a typical course of 8–12 treatments (each treatment takes approximately 15 minutes) administered bi- or tri-weekly. Perhaps the most discouraging aspect of ECT is that greater than half of the successfully treated ECT patients will relapse into clinical depression in less than a year. Sackeim, H. A., Prudic, J., Devanand, D. P., Decina, P., and Malitz, S. (1990), "The Impact of Medication Resistance and Continuation Pharmacotherapy on Relapse Following Response to Electroconvulsive Therapy in Major Depression," *J Clin Psychopharmacol* 10: 96–104.

Psychotherapy

Psychotherapy involves talking with a trained mental health professional, such as a psychiatrist. These therapies help a patient gain insight into and resolve their problems through verbal exchange with their psychiatrist. One of the short-term therapies effective in treating both depressive disorders and anxiety disorders is the cognitive-behavioral therapy. Treatments tend to be more successful for mild and moderate forms of depressive and anxiety disorders and usually require medication or ECT treatment along with, or preceding, psychotherapy for the best outcome.

Psychoactive Drugs

The same drugs most commonly used to manage depressive disorders are used to treat anxiety disorders. There are several types of antidepressant medications used to treat depressive and anxiety disorders. Most of the oral antidepressive medications used today are designed to increase the levels of specific monoamine neurotransmitters in the brain (e.g., norepinephrine, serotonin, and dopamine). More recent pharmacologic strategies have focused on antagonizing the effects of specific peptidergic neurotransmitters in the brain, namely corticotropin-releasing hormone and substance P.

Thyrotropin Releasing Hormone

Thyrotropin-releasing hormone (TRH) is a hypothalamic tripeptide hormone which stimulates the pituitary gland to secrete thyroid-stimulating hormone. In addition, TRH functions as a neurotransmitter and neuromodulator in many areas of the central nervous system. TRH (also called protirelin) is a drug that has been studied in the past for the treatment of depression but was shown to produce unpredictable responses when administered parenterally (IV or SQ). Itil, T. M., Patterson, C. D., Polvan, N., Bigelow, A. and Bergey, B. (1975), "Clinical and CNS Effects of Oral and IV Thyrotropin-Releasing Hormone in Depressed Patients," *Dis Nerv Sys* 2: 529–536; Prange, A. J., Wilson, I. C., Lara, P. D., Alltop, L. B. and Breese, G. R. (1972), "Effects of Thyrotropin-Releasing Hormone in Depression," *Lancet* 2:999–1002. Because TRH is a tripeptide that is subject to proteolysis in the upper gastrointestinal tract, it cannot be administered orally.

TRH has been administered directly to the CNS for the treatment of a psychiatric disease. Callahan, A. M., Frye, M. A., Marangell, L. B., George, M. S., Ketter, T. A., L'Herrou, T. A. and Post, R. M., (1997), "Comparative Antidepressant Effects of Intravenous and Intrathecal Thyrotropin-Releasing Hormone: Confounding Effects of Tolerance and Implications for Therapeutics," *Biol. Psychiatry* 41: 264–272; Marangell, L. B., George, M. S., Callahan, A. M., Ketter, T. A., Pazzaglia, P. J., L'Herrou, T. A., Leverich, G. S. and Post, R. M., (1997), "Effects of Intrathecal Thyrotropin-Releasing Hormone (Protirelin) in Refractory Depressed Patients," *Arch. Gen. Psychiatry* 54: 214–222. This treatment, a single intrathecal bolus of TRH, was successfully used to treat refractory depression in 7 out of 10 patients. With the exception of sleep deprivation, this is the only therapy that has been demonstrated to produce a rapid (<24 hr) and dramatic improvement in the symptoms of severe depression. However, the study did not involve varying the dosage of the therapeutic substance.

Serotonin Agonists

In the case of serotonergic agonists, direct CNS delivery would be of benefit because many of them only poorly penetrate the blood-brain barrier.

A serotonin agonist, sumatriptan, although not used to treat depression has been used in research studies related to depression and other psychiatric diseases. Stem et al., describes the chronic use of parenteral sumatriptan to treat patients with refractory obsessive-compulsive disorder (OCD). Stem, L., Zohar, J., Cohen, R., and Sasson, Y., (1998), "Treatment of Severe, Drug Resistant Obsessive Compulsive Disorder with the $5HT_{1D}$ agonist Sumatriptan," *Eur Neuropsychopharmacol* 8: 325–328. Although these patients experienced only modest reductions in their OCD behaviors, they demonstrated significant improvements in their symptoms of depression as measured by the Hamilton scale. Because sumatriptan does not readily penetrate the blood-brain barrier, intrathecal delivery would be expected to significantly increase the efficacy of this agent. Saxena, P. R., (1992), "Migraine Therapy and 5-HT Receptor Activity," *J Neurol* 238: S36–S37. Arranz et al, reported on reduced $5HT_{1D}$ receptor density and binding affinity in brain tissues of suicide victims. Arranz, B., Erikson, A., Mellerup, E., Plenge, P. and Marcusson, J., (1994), "Brain $5HT_{1A}$, $5HT_{1D}$ and $5HT_2$ Receptors in Suicide Victims," *Biol Psychiatry* 35:457–463.

Although serotonin (5-HT) is not available as a pharmaceutical agent, certain receptor subtype selective agonists are (e.g., sumatriptan, Imitrex® manufactured by Glaxo Wellcome, $5-HT_1$ receptor selective agonist currently formulated for injection, 12 mg/ml in saline with no preservatives, indicated use: migraines). The $5-HT_{1A}$-receptor has been implicated as a major receptor involved in the antidepressive response to SSRIs. Deakin, J. F. W., (1998), "$5HT_{1A}$ Receptors, Depression, and Anxiety," *Pharmacol Biochem Behav* 29: 819–830.

Buspirone, an anxiolytic drug, produces at least part of its effect by activation of $5-HT_{1A}$ receptors. Sussman, N., (1994), "The Potential Benefits of Serotonin Receptor-Specific Agents," *J Clin Psychiatry* 55: 45–51. Mirtazapine, a newly FDA-approved antidepressant (AD), blocks two types of serotonin receptors ($5-HT_2$ and $5-HT_3$,). Feighner, J. P., (1999), "Mechanism of Action of Antidepressant Medications," *J Clin Psychiatry* 60: 4–13. Trazodone is another antidepressant that acts to inhibit neuronal reuptake of serotonin and also antagonizes $5-HT_2$ receptors. Ruoff, G. E., (1996), "Depression in the Patient with Chronic Pain," *J Fam Pract* 43: S25–S34.

Nefazodone, a newer AD, inhibits both $5-HT_2$ and $5-HT_3$ receptors. These antidepressive mechanisms suggest that activation of $5-HT_2$ and $5-HT_3$ receptors are not involved in the same biochemical pathways associated with selective serotonin reuptake inhibitor (SSRI)-induced efficacy and lends further support to the intrathecal use of sumatriptan (i.e., serotonin-like efficacy without the side effects). The antidepressive effects of SSRIs appears to involve $5-HT_1$ receptors (1A, 1B, and 1D); insomnia and sexual dysfunction effects have been attributed to $5-HT_2$ receptor activation and GI side effects have been attributed to $5-HT_3$ receptor activation. Thase, M. E., Frazer, A., Gorman, J. M., Hirschfeld, R. M. and Roose, S. P., (2000), "Pharmacotherapy of Depression: New Strategies," *A Symposium of the American Psychiatric Association* 2000 *Annual Meeting*.

Adrenergic Agonists

The majority of antidepressants presently used are designed to affect two major neurotransmitter systems of the brain, norepinephrine and serotonin. Antidepressants inhibit the neuronal reuptake (tricyclic antidepressants—norepinephrine (NE) and 5-HT, SSRIs—just 5-HT, selective norepinephrine reuptake inhibitors—just NE) or degradation (monoamine oxidase inhibitors) of one or both of these neurotransmitters. Although this is the common "first step" pharmacologic effect of antidepressants that leads to a corresponding increase in synaptic neurotransmitter concentrations, the precise biochemical pathways which lead to the ultimate therapeutic outcome have yet to be elucidated. It also is not appreciated why this pharmacologic first step occurs almost immediately after the medication is taken, whereas the patient does not experience relief from his/her symptoms of depression for weeks afterwards.

Intrathecal administration of NE has been studied in animal models of analgesia, spinal cord injury, and motor reflexes. Howe, J. and Yaksh, T. L., (1982), "Changes in Sensitivity to Intrathecal Norepinephrine and Serotonin after 6-Hydroxydopamine, 5,6-Dihydroxytryptamine or Repeated Monoamine Administration," *J Pharmacol Exp Ther* 220: 311–321; Milne, B., Cervenko, F., Jhamandas, K., Loomis, C. and Sutak, M., (1985), "Analgesic and Tolerance to Intrathecal Morphine and Norepinephrine Infusion via Implanted Mini-Osmotic Pumps in the Rat," *Pain* 22: 165–172; Minor, B. G., Persson, M. L., Post, C., Jonsson, G. and Archer, T. (1988), "Intrathecal Noradrenaline Restores 5-Methoxy-N,N-demthyltryptamine Induced Antinociception Abolished by Intrathecal 6-Hydroxydopamine," *J Neural Transm* 72: 107–120; Brustein, E. and Rossignol, S. (1999), "Recovery of Locomotion After Ventral and Ventrolateral Spinal Lesions in the Cat: Effects of Noradrenergic and Serotoninergic Drugs," *J Neurophysiol* 81: 1513–1530; Wiesenfield-Hallin, Z., (1987), "Intrathecal Noradrenaline has a Dose-Dependent Inhibitory or Facilitory Effect on the Flexion Reflex in the Rat," *Acta Physiol Scand* 130: 507–511. In these studies, no undesirable or unpredicted responses were attributed to intrathecal NE administration.

Recent theories proposed on the biochemical mechanisms of ADs focus on adrenoceptors and the enzyme responsible for NE synthesis, tyrosine hydroxylase. Leonard, B. E., (1997), "Noradrenaline in Basic Models of Depression," *Eur Neuropsychopharmacol* 7: 511–516. Many ADs produce a decrease in function and/or adrenoceptor density as well as decreases in the tyrosine hydroxylase levels in the brain. Thase, M. E., Frazer, A., Gorman, J. M., Hirschfeld, R. M. and Roose, S. P., (2000), "Pharmacotherapy of Depression: New Strategies," *A Symposium of the American Psychiatric Association* 2000 *Annual Meeting*. These are biochemical endpoints which may be accomplished more effectively by direct NE infusion.

The direct infusion of NE as opposed to relying on oral ADs to inhibit neuronal NE uptake may provide several advantages. Both methods result in increasing the amount of extracellular NE, but traditional ADs are limited by the endogenous pool of NE available in the vesicles of the nerve terminals. By providing an exogenous source of the transmitter, the concentration of NE may be increased above the endogenous limit. Those skilled in the art will realize that in pharmacology drugs that exert their effects indirectly (i.e., are dependent on the causing the release of or inhibiting the degradation of a primary endogenous molecule) are usually limited in the maximum effect they can produce. This efficacy limitation is a direct result of the limited pool of endogenous agonist. It is also conceivable that the lack of an adequate clinical response to oral reuptake inhibitors in select patient populations is a result of depleted or inaccessible pools of NE within the terminals of the presynaptic neurons. It is reasonable to assume that only with an intact endogenous supply of presynaptic NE can the initial pharmacologic impact of reuptake inhibition be expected to occur. An exogenous supply of NE would be able to circumvent this "theoretical" problem. Using exogenous NE may potentially speed recovery and provide efficacy in patients who have previously been shown to be resistant to oral therapy.

Corticotropin-Releasing Factor Antagonists

Corticotropin-releasing factor (CRF) is an endogenous 41-amino-acid peptide that is produced in the brain and which is critical for mediating responses to stress. It is released by the hypothalamus and serves to activate the pituitary and adrenal glands resulting in the release of epinephrine and cortisol into the blood. It is know in the art of psychiatry that patients with depression have elevated plasma cortisol levels as a result of an overactive hypthalamic-pituitary-adrenal (HPA) axis. It is also appreciated that stress, especially prolonged stress and early-childhood stress, can induce depression. Since CRF is the initial chemical mediator of the stress response, drugs which block the effect of CRF may block this stress cascade and be useful in treating depression and anxiety disorders. Published scientific literature supports this but a successful therapeutic that works by blocking this pathway has yet to make into the clinic.

Companies are pursuing agents which can be administered orally similar to all the other drugs which are currently marketed for depression. A general type of CRF antagonist that can block the relevant receptors but that cannot be given orally or cross the blood-brain barrier are peptide antagonists. Although peptide antagonists are often used in research and function quite effectively to block the targeted receptor, because they would be digested in the gastrointestinal tract if given orally and not cross the blood-brain barrier to reach their site of action if given IV or SQ, these peptidergic agents have not been been pursued as viable therapeutic candidates.

Substance P Antagonists

Substance P is an 11-amino-acid endogenous peptide neurotransmitter that is known to be involved in the transmission of pain information to the central nervous system. Substance P produces its effects by activating cell-surface receptors known as neurokinin-1 (NK-1) receptors. Recently, it has been appreciated both in animal studies and clinical trials that substance P places an important role in mediating stress responses and that antagonism of the NK-1 receptors may have positive effects in treating mood and anxiety disorders. Kramer, M. S., (1998), "Distinct Mechanism for Antidepressant Activity by Blockade of Central Substance P Receptors," *Science* Volume 281 September 11, 1640–1625. Substance P concentrations are especially high in the brain structure known as the amygdala, an important area that regulates mood and anxiety.

SUMMARY OF THE INVENTION

One or more of the above-mentioned deficiencies in the art are satisfied by the method and system of the present invention of operating a programmable pump for the delivery of at least one therapeutic substance into the cerebrospinal fluid (CSF) of a patient for the treatment of depressive or anxiety disorders. The invention involves the use of at least one therapeutic substance to treat a depressive or an anxiety disorder in a patient. For example, a catheter is implanted in a patient, the catheter having a proximal end coupled to a programmable pump and a distal end for infusing the at least one therapeutic substance. The distal end of the catheter is located at or in the cerebrospinal fluid of a patient. The programmable pump is operated to deliver a first rate of the at least one therapeutic substance into the cerebrospinal fluid of the patient to treat the depressive or anxiety disorder. The programmable pump is regulated in response to a treatment plan to deliver a second rate of the at least one therapeutic substance in order to treat the depressive or anxiety disorder.

In addition, a sensor implanted in a patient may be used in combination with a programmable pump and a catheter to deliver at least one therapeutic substance to treat a depressive or an anxiety disorder in the patient. The sensor is implanted in the patient for generating a sensor signal detecting the extent of the depressive or anxiety disorder in the patient. The programmable pump is operated to deliver a first rate of the at least one therapeutic substance into the cerebrospinal fluid of the patient. The programmable pump is regulated in response to the sensor signal to deliver a second rate of the at least one therapeutic substance to treat the depressive or anxiety disorder.

Thus, the programmable pump can adjust the second rate of the at least one therapeutic substance to optimize treatment. The sensor can provide signals on a periodic or continuous basis so that the programmable pump can adjust the delivery of the at least one therapeutic substance to the patient. Additionally, the use of a programmable pump as disclosed in this invention allows complex dosage schemes as opposed to individual bolus doses to avoid the potential effects of tolerance and accommodate the changing clinical status of patients.

These and other advantages and features of the invention will become apparent upon reading and following the detailed description and referring to the accompanying drawings which like numbers refer to like parts throughout.

DETAILED DESCRIPTION OF THE PREFERRED EMBODIMENTS

Figure 1:
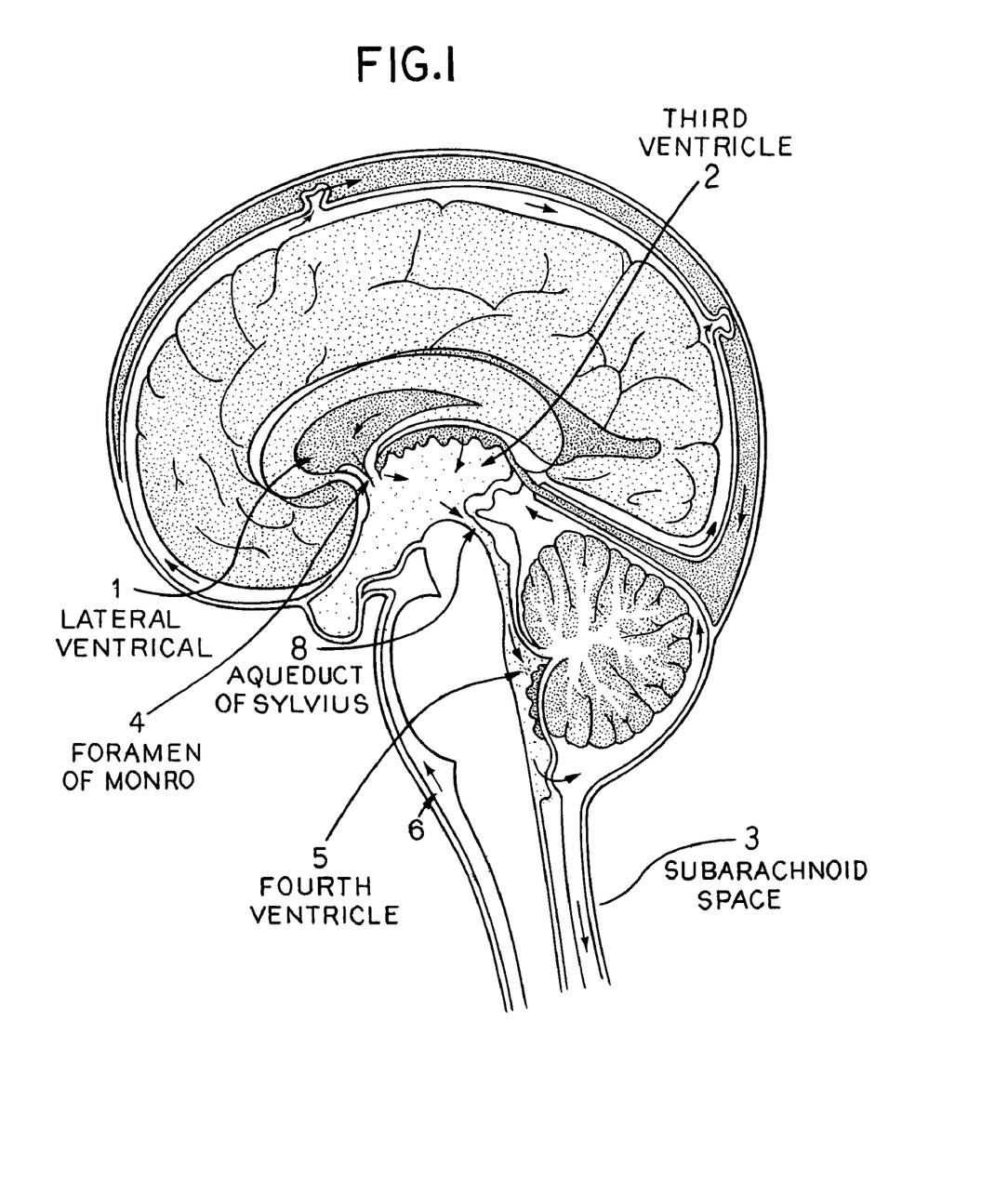
FIG. 1 is a diagrammatic illustration of the flow of cerebrospinal fluid in the subarachnoid space of a patient.

As illustrated in FIG. 1, the central nervous system (brain and spinal cord) is surrounded by cerebrospinal fluid 6 contained within the subarachnoid space 3. In addition, cerebrospinal fluid 6 is also contained in the four ventricles of the brain: two lateral ventricles 1, the third ventricle 2, and the fourth ventricle 5. The lateral ventricles 1 are connected to the third ventricle 2 via the foramen of Monro 4; the third ventricle 2 is connected to the fourth ventricle 5 via the aqueduct of Sylvius 8. The arrows within the subarachnoid space 3 in FIG. 1 indicate cerebrospinal fluid 6 flow.

The subarachnoid space 3 is a compartment within the central nervous system that contains cerebrospinal fluid 6. The cerebrospinal fluid 6 is produced in the ventricular system of the brain and communicates freely with the subarachnoid space 3 via the foramina of Magendie and Luschka.

Given the limited efficacy of other conventional treatments, as discussed in the background section, intrathecal delivery of therapeutics with the use of a programmable pump into the cerebrospinal fluid 6 offers the potential to treat a large portion of severely affected patients with depressive and anxiety disorders who currently have limited options. Depressive disorders that may be treated by intrathecal delivery of therapeutic substances through the use of a programmable pump in accordance with the present invention comprise refractory depression, dysthymia, or bipolar disorder. Similarly, anxiety disorders that may be treated by intrathecal delivery of therapeutic substances through the use of a programmable pump in accordance with the present invention comprise panic disorder, obsessive-compulsive disorder, generalized anxiety disorder, or social phobia.

Intrathecal delivery of therapeutics into the cerebrospinal fluid is less invasive than intraparenchymal (direct tissue) delivery of therapeutics. In addition, intrathecal delivery of therapeutics may not require the need for a neurosurgeon as the delivery of the therapeutics does not require delivery to a direct brain target. Numerous other physicians may be qualified to insert a catheter into the lumbar subarachnoid space of the spinal column in order to initiate intrathecal therapeutic delivery.

Figure 2:
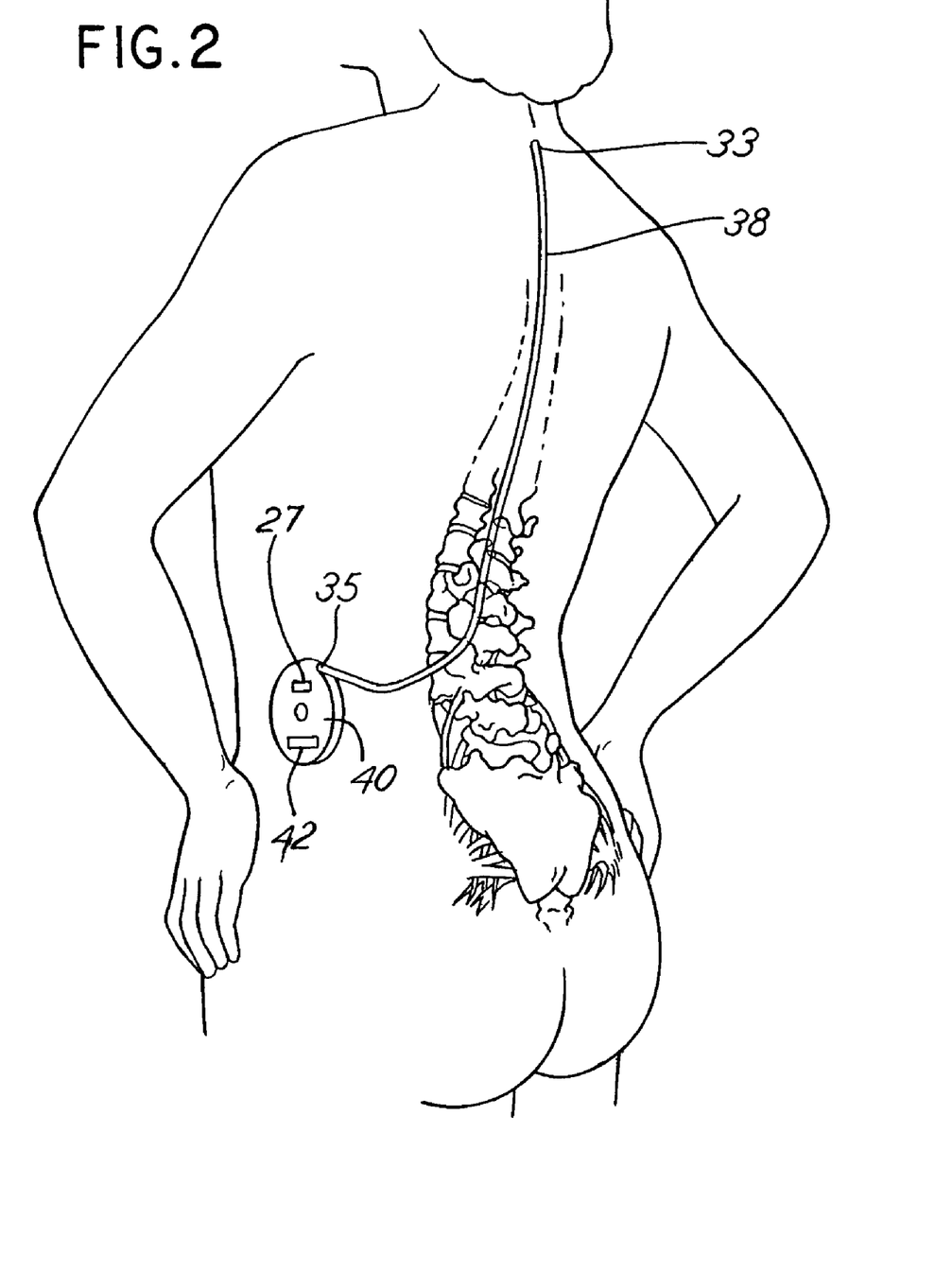
FIG. 2 is a diagrammatic illustration of a programmable pump and a catheter implanted in a patient according to the present invention.
Figure 3:
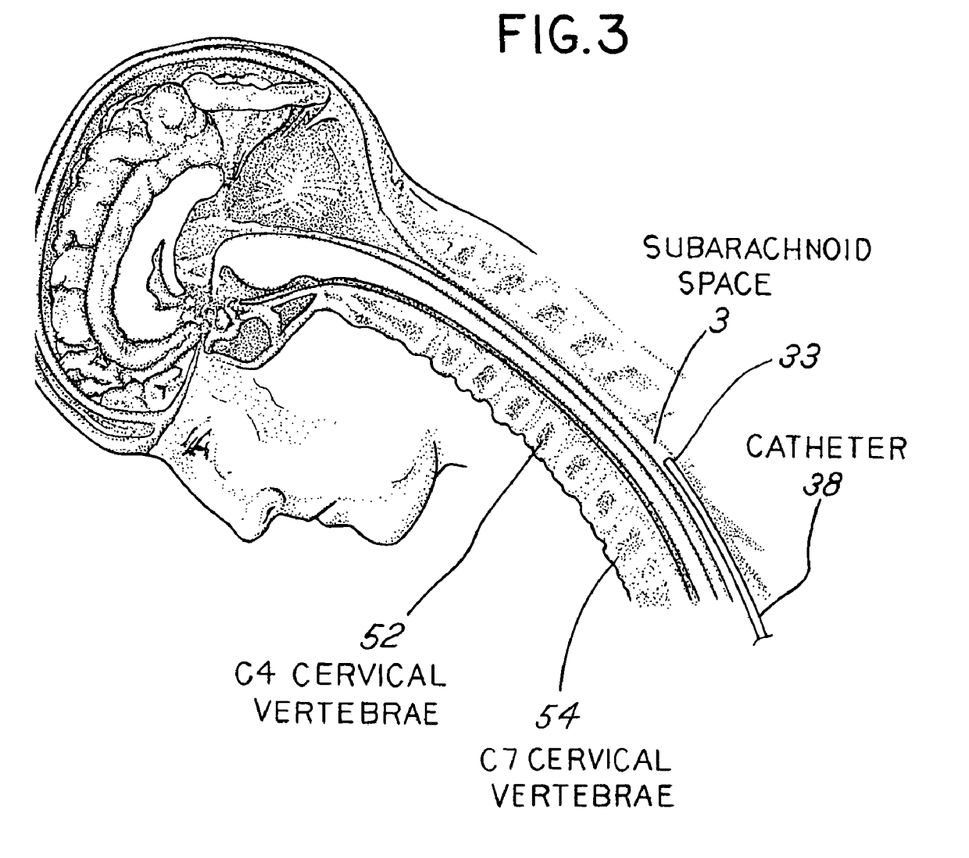
FIG. 3 is a diagrammatic illustration of a catheter implanted in a patient's subarachnoid space for the delivery of a therapeutic substance into the cerebrospinal fluid.

FIG. 2 illustrates a programmable pump 40 and a catheter 38 in accordance with the present invention. The programmable pump 40 and catheter 38 may be implanted in a patient after diagnosis of a depressive or anxiety disorder. The programmable pump 40 may take the form of a Synchromed® infusion pump as manufactured by Medtronic, Inc. of Minneapolis, Minn. A reservoir 27 that contains the therapeutic substance to be delivered is housed in programmable pump 40. The location of programmable pump 40 implantation is one in which the implantation interferes as little as practicable with patient activity, such as subcutaneous in the lower abdomen. The proximal end 35 of catheter 38 is connected to programmable pump 40. Catheter 38 is a flexible tube with a lumen typically running the length of catheter 38. The distal end 33 of catheter 38 is positioned to infuse a therapeutic substance or substances into the target area of CSF of the patient. The target area of CSF of the patient may be the subarachnoid space 3 between the fourth cervical vertebrae (C4) 52 and seventh cervical vertebrae (C7) 54, as shown in FIG. 3. The programmable pump 40 is operated to discharge a predetermined dosage of therapeutic or therapeutics into the CSF of the patient.

Figure 7:
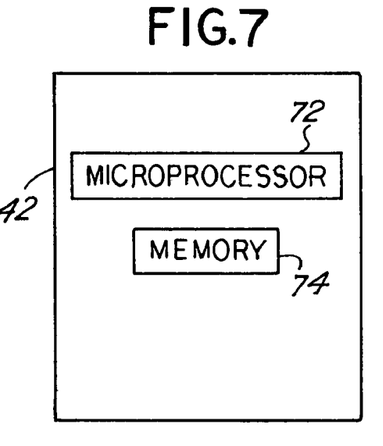
FIG. 7 is diagrammatic illustration of a control unit in accordance with the present invention.

The programmable pump 40 is operatively coupled to and responsive to electrical signals delivered to it from a control unit 42. Electrical signals from the control unit 42 could for example, start and stop the programmable pump 40. As shown in FIG. 7, control circuitry within the control unit 42 would typically include a microprocessor 72 or similar device, and memory 74. In addition, control unit 42 contains the appropriate interface circuitry well known to those skilled in the art to couple microprocessor 72 to the programmable pump 40. Microprocessor 72 controls the amount of therapeutic substance administered to the patient according to therapy program instructions stored in memory 74. Memory 74 has the ability to store and retrieve the therapy program and data.

The programming of the programmable pump 40 may be accomplished with an external programmer/control unit via telemetry. The controlled amount of therapeutic or therapeutics may be delivered over a specified time period. With the use of the programmable pump 40, different dosage regimens may be programmed for a particular patient. Additionally, different therapeutic dosages can be programmed for different combination of therapeutics. The programmable pump 40 gives the clinicians the ability to program different rates of therapeutic delivery that may be required during the course of a day or during the course of a treatment regiment. For example, a first rate of at least one therapeutic substance is delivered into the CSF of patient according to predefined therapy plan to treat a depressive or an anxiety disorder. The first rate of therapeutic substance delivered may correspond to a certain time of day in which a patient is usually more active, daytime. Next, in accordance with the predefined therapy plan, a second rate of at least one therapeutic substance may be delivered corresponding to a different time of day in which a patient is less active, nighttime. As one skilled in the art will realize, programmable pump 40 allows for the delivery of complex therapeutic delivery schemes as opposed to fixed rate therapeutic delivery. These complex delivery schemes that may contain a number of different and changing therapeutic delivery rates such as a first, second, and third rate of delivery.

The therapeutic substance delivered by programmable pump 40 to treat the depressive or an anxiety disorder may comprise a serotonin agonist. The serotonin agonist may comprise a 5-HT$_1$ agonist. The 5-HT$_1$ agonist may comprise sumatriptan or buspirone. Alternatively, the therapeutic substance delivered by programmable pump 40 to treat the depressive or an anxiety disorder may comprise an adrenergic agonist. The adrenergic agonist may comprise norepinephrine, epinephrine, and/or isoproterenol.

Programmable pump 40 may also deliver a corticotropin-releasing factor antagonist to treat the depressive or an anxiety disorder. The corticotropin-releasing factor antagonist may comprise astressin, D-pheCRF (12–41), and/or alpha-helicalCRF (9–41).

Additionally, programmable pump 40 may deliver a therapeutic substance such as a substance P antagonist to treat the depressive or an anxiety disorder. The substance P antagonist may comprise a peptide antagonist such as a neurokinin 1 antagonist.

Also, programmable pump 40 may deliver a thyrotropin-releasing hormone receptor agonist (TRH-RA) to treat the depressive or anxiety disorder. The TRH-RA may be selected from the group consisting of TRH, MK771, (NS-3) CG3703, TA0910, YM14673, RX77368, RX74355, 2,4-diodo(Im)-TRH, 4(5)-$NO_2$(Im)-TRH, CG3509, CG3703, TRH-Gly and PS4.

The therapeutic substance may also be delivered into the CSF through a ventricle of the brain. Delivery of a therapeutic substance through a ventricle of the brain may be advantageous especially as the structures of the brain, especially the structures of the limbic system including the amygdala, the locus coeruleus, and the hypothalamus are the ultimate therapeutic targets.

Figure 4:
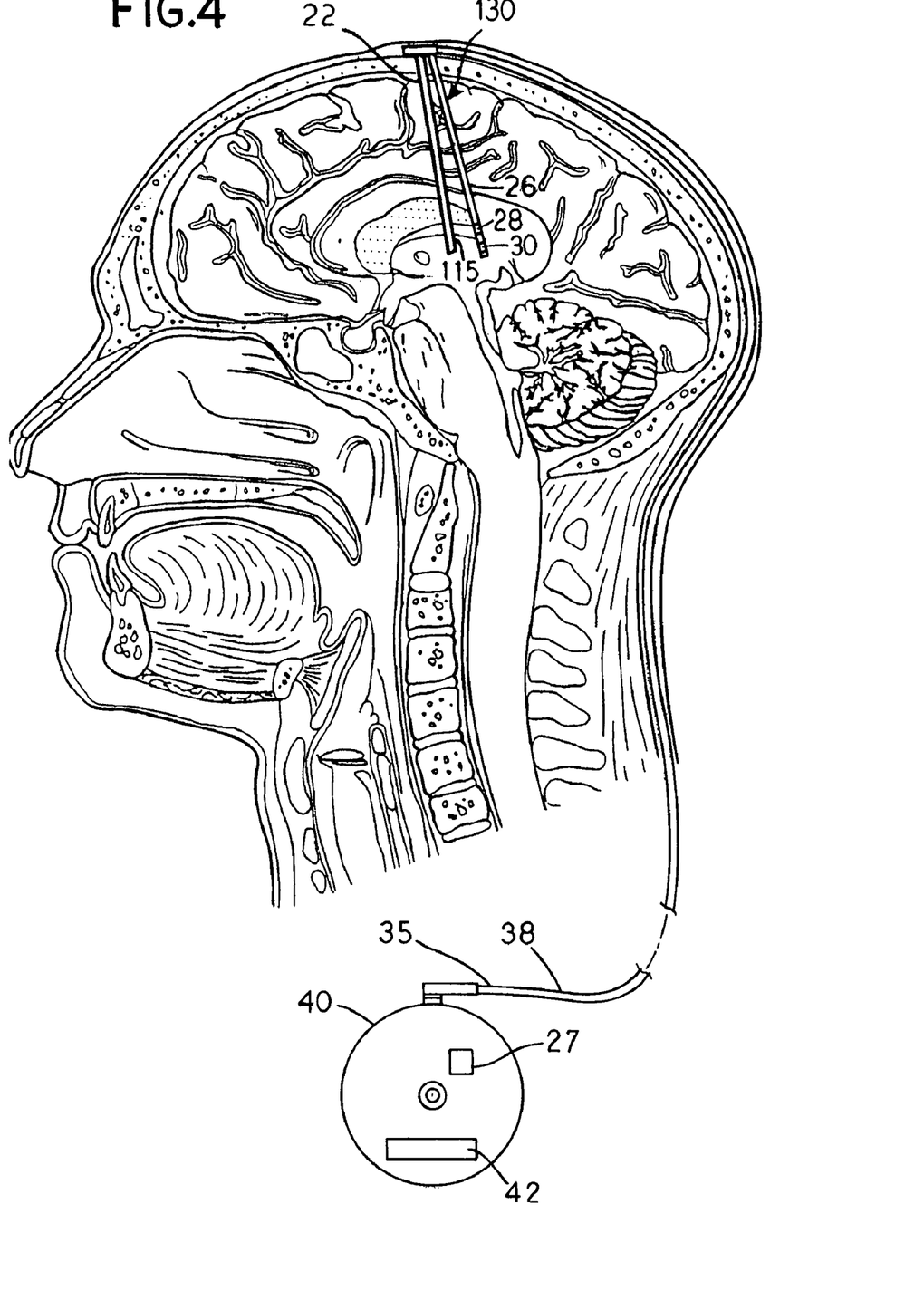
FIG. 4 is a diagrammatic illustration of a catheter and a sensor implanted in a patient's brain, the catheter and sensor attached to a pump for the delivery of a therapeutic substance in accordance with another embodiment of the invention.

Referring to FIG. 4, catheter 38 is positioned to deliver a therapeutic substance to a specific infusion site in the brain. The distal end of catheter 38 terminates in a cylindrical hollow tube 22 having a distal end 115. The distal end 115 of catheter 38 may be implanted in a ventricle of the brain to provide the therapeutic substance into a patient's CSF. The proximal end 35 of catheter 38 is coupled to the programmable pump 40.

A sensor 130 is implanted into a portion of a patient's central nervous system. As shown in FIG. 4, sensor 130 may comprise a sensing lead 26 having two sensing electrodes 28 and 30 located in the patient's brain to measure the electrical activity of a patient's hypothalamus. Sensor 130 may be placed in the third ventricle of a patient's brain to measure the electrical activity of the hypothalamus.

Another form of sensor 130 may be a chemical sensor that is capable of detecting the amount of depression-associated analyte quantified in the CSF or plasma. As one skilled in the art will realize, one of the most reproducible finding in all of psychiatric research is the increase in the hypothalamo-pituitary-adrenal axis activity in depression. Keller, M. B., Schatzberg, A. F., Charney, D. S., Krishnan, K. R., Weissman, M. M. and Nemeroff, C. B. (2000), "Novel Treatments of Depression," *A symposium held at the* 2000 *Annual Meeting of the APA*. Accordingly, the level of corticotropin-releasing hormone in the CSF, or cortisol or epinephrine in the plasma, may be detected in order to regulate the amount of therapeutic substance dispensed from the programmable pump.

Figure 5:
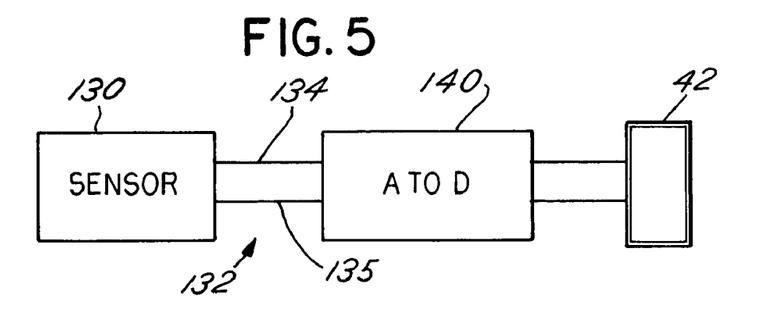
FIG. 5 is a schematic diagram of a sensor and a converter in accordance with the present invention.

Sensor 130 may be used with a control loop feedback system in order to automatically determine the amount of therapeutic substance delivery necessary to treat the depressive or anxiety disorder. Referring to FIG. 5, the output of sensor 130 may be connected to a cable 132 comprising conductors 134 and 135. Conductors 134 and 135 may be connected to the input of an analog-to-digital converter 140. The output of the analog-to-digital converter 140 may be connected to control unit 42. Electrical signals from the control unit 42 could, for example, regulate the rate of therapeutic substance delivery.

Figure 6:
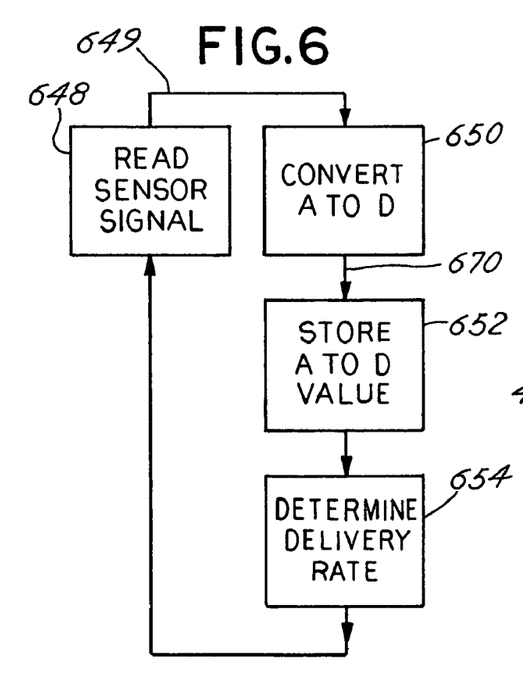
FIG. 6 is a flow chart describing closed loop feedback in accordance with the present invention.

FIG. 6 illustrates a therapeutic program for use with the present invention. In step 648, a sensor signal 649 is received by analog-to-digital converter 140. In step 650, the sensor signal 649 is converted from an analog to a digital signal in analog-to-digital converter 140. The digital signals from the analog-to-digital converter 140 are read by control unit 42. The value of the analog-to-digital output 670 may be stored in memory 74 as shown in step 652. Next, control unit 42 determines the proper therapeutic delivery rate in step 654. The delivery rate determined in step 654 may be in accordance with predefined limits programmed into programmable pump 40 by a clinician at the onset of the therapeutic substance delivery. Control unit 42 then regulates pump 40 so that pump 40 delivers the therapeutic rate determined by step 654. Finally, another sensor signal 649 is generated by sensor 130 and the process begins again at step 648.

The embodiments of the invention, and the invention itself, are now described in such full, clear, concise and exact terms to enable a person of ordinary skill in the art to make and use the invention. To particularly point out and distinctly claim the subject matters regarded as invention, the following claims conclude this specification. To the extent variations from the preferred embodiments fall within the limits of the claims, they are considered to be part of the invention, and claimed.

I claim:

1. A method of using a thyrotropin-releasing hormone receptor agonist to treat a depressive or an anxiety disorder in a patient by means of a programmable pump and a catheter, the catheter having a proximal end coupled to the programmable pump and a distal end for infusing the thyrotropin-releasing hormone receptor agonist, the method comprising the steps of:

implanting the catheter so that the distal end of the catheter is located in cerebrospinal fluid of the patient;
   operating the programmable pump to deliver a first rate of the thyrotropin-releasing hormone receptor agonist into cerebrospinal fluid of the patient; and
   regulating the programmable pump to deliver a second rate of the thyrotropin-releasing hormone receptor agonist in order to treat the depressive or the anxiety disorder.

2. The method of claim 1, wherein the thyrotropin-releasing hormone receptor agonist comprises thyrotropin-releasing hormone.

3. The method of claim 1, wherein the depressive disorder comprises refractory depression.

4. The method of claim 1, wherein the depressive disorder comprises dysthymia.

5. The method of claim 1, wherein the depressive disorder comprises bipolar disorder.

6. The method of claim 1, wherein the anxiety disorder comprises panic disorder.

7. The method of claim 1, wherein the anxiety disorder comprises obsessive compulsive disorder.

8. The method of claim 1, wherein the anxiety disorder comprises generalized anxiety disorder.

9. The method of claim 1, wherein the thyrotropin-releasing hormone receptor agonist is selected from the group consisting of MK771, (NS-3) CG3703, TA0910, YM14673, RX77368, RX74355, 2,4-diodo(Im)-TRH, 4(5)-$NO_2$(Im)-TRH. CG3509, CG3703, TRH-Gly and PS4.

* * * * *